United States Patent
Alon et al.

(10) Patent No.: US 10,398,555 B2
(45) Date of Patent: Sep. 3, 2019

(54) MAGNETICALLY COUPLED CINCHING OF A LOOP INSTALLED IN A VALVE ANNULUS

(71) Applicant: Cardiac Implants LLC, Tarrytown, NY (US)

(72) Inventors: David Alon, Zichron Yaakov (IL); Nimrod Meller, Kfar Yehoshua (IL)

(73) Assignee: Cardiac Implants LLC, Tarrytown, NY (US)

( * ) Notice: Subject to any disclaimer, the term of this patent is extended or adjusted under 35 U.S.C. 154(b) by 269 days.

(21) Appl. No.: 15/003,731

(22) Filed: Jan. 21, 2016

(65) Prior Publication Data
US 2016/0135953 A1 May 19, 2016

Related U.S. Application Data

(63) Continuation-in-part of application No. 14/364,060, filed as application No. PCT/IB2012/057138 on Dec. 10, 2012, now Pat. No. 10,143,553.
(Continued)

(51) Int. Cl.
*A61F 2/24* (2006.01)

(52) U.S. Cl.
CPC .......... *A61F 2/2466* (2013.01); *A61F 2/2445* (2013.01)

(58) Field of Classification Search
CPC ........ A61F 2/2445; A61F 2/24; A61F 2/2409; A61F 2/2442; A61F 2/2448; A61F 2/2451; A61F 2/2466
See application file for complete search history.

(56) References Cited

U.S. PATENT DOCUMENTS

| | | | | |
|---|---|---|---|---|
| 688,592 | A | * 12/1901 | Chadwick | .......... A62B 35/0025 182/6 |
| 4,042,979 | A | 8/1977 | Angell | |

(Continued)

FOREIGN PATENT DOCUMENTS

| | | |
|---|---|---|
| CN | 1684644 A | 10/2005 |
| CN | 2782049 | 5/2006 |

(Continued)

OTHER PUBLICATIONS

Office Action dated Aug. 18, 2017, in Chinese Patent Application 201610004737.X (with translation).
(Continued)

*Primary Examiner* — Elizabeth Houston
*Assistant Examiner* — Lindsey Bachman
(74) *Attorney, Agent, or Firm* — Potomac Law Group, PLLC

(57) ABSTRACT

The diameter of an annulus in a patient (e.g., the mitral valve annulus) can be reduced using a tissue engaging member that is installed on the annulus and an actuator that is implanted into the patient's body. The tissue engaging member has anchors used to implant the tissue engaging member into the annulus, and a cinching loop runs through the tissue engaging member. The cinching loop terminates onto cinching wires. Preferably, tissue healing is used to enhance the bond between the tissue engaging member and the annulus. The actuator, which can be actuated from outside the patient's body, pulls the cinching wires in a proximal direction while holding the distal end of the cinching wires in close proximity to each other, so as to cause a reduction in the diameter of the cinching loop. This will cause a corresponding reduction in the diameter of the annulus.

21 Claims, 9 Drawing Sheets

Related U.S. Application Data

(60) Provisional application No. 62/107,437, filed on Jan. 25, 2015, provisional application No. 61/683,736, filed on Aug. 16, 2012, provisional application No. 61/569,304, filed on Dec. 12, 2011.

(56) References Cited

U.S. PATENT DOCUMENTS

| | | |
|---|---|---|
| 5,860,951 A | 1/1999 | Eggers et al. |
| 6,283,961 B1 | 9/2001 | Underwood et al. |
| 6,306,163 B1 | 10/2001 | Fitz |
| 6,575,971 B2 | 6/2003 | Hauck et al. |
| 6,626,930 B1 | 9/2003 | Allen et al. |
| 6,656,221 B2 | 12/2003 | Taylor et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 7,314,485 B2 | 1/2008 | Mathis |
| 7,588,582 B2 | 9/2009 | Starksen et al. |
| 8,430,926 B2 | 4/2013 | Kirson |
| 2002/0095175 A1* | 7/2002 | Brock .................. A61B 34/20 606/205 |
| 2004/0073302 A1 | 4/2004 | Rourke et al. |
| 2004/0102839 A1 | 5/2004 | Cohn et al. |
| 2004/0102840 A1 | 5/2004 | Solem et al. |
| 2004/0220610 A1 | 11/2004 | Kreidler et al. |
| 2004/0243227 A1 | 12/2004 | Starksen et al. |
| 2005/0070924 A1 | 3/2005 | Schaller et al. |
| 2005/0107812 A1 | 5/2005 | Starksen et al. |
| 2005/0119523 A1 | 6/2005 | Starksen et al. |
| 2005/0216078 A1 | 9/2005 | Starksen et al. |
| 2005/0273138 A1 | 12/2005 | To et al. |
| 2000/6002575 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0129188 A1 | 6/2006 | Starksen et al. |
| 2007/0016286 A1 | 1/2007 | Herrmann et al. |
| 2007/0016287 A1* | 1/2007 | Cartledge ............ A61F 2/2448 623/2.11 |
| 2007/0244554 A1 | 10/2007 | Rafiee et al. |
| 2008/0051823 A1* | 2/2008 | Makower ........... A61B 17/1285 606/192 |
| 2008/0177380 A1* | 7/2008 | Starksen ............. A61B 17/064 623/2.11 |
| 2008/0177382 A1 | 7/2008 | Hyde et al. |
| 2008/0262609 A1 | 10/2008 | Gross et al. |
| 2009/0076597 A1* | 3/2009 | Dahlgren ............ A61B 17/7016 623/2.1 |
| 2009/0093890 A1* | 4/2009 | Gelbart .................. A61B 17/68 623/24 |
| 2009/0177277 A1 | 7/2009 | Milo |
| 2009/0287304 A1* | 11/2009 | Dahlgren ............ A61B 17/0401 623/2.37 |
| 2010/0249920 A1 | 9/2010 | Bolling et al. |
| 2011/0106247 A1 | 5/2011 | Miller et al. |
| 2011/0301701 A1 | 8/2011 | Padala |
| 2011/0230961 A1 | 9/2011 | Langer |
| 2012/0010700 A1 | 1/2012 | Spenser |
| 2013/0331930 A1 | 12/2013 | Rowe et al. |
| 2014/0309730 A1 | 10/2014 | Alon et al. |
| 2016/0120645 A1 | 5/2016 | Alon |

FOREIGN PATENT DOCUMENTS

| | | | |
|---|---|---|---|
| CN | 102215784 A | | 10/2011 |
| JP | 2007514455 A | | 6/2007 |
| JP | 2010511469 A | | 4/2010 |
| WO | 2005025644 A2 | | 3/2005 |
| WO | 2006052687 A1 | | 5/2006 |
| WO | 2008068756 | | 6/2008 |
| WO | 2009120764 | | 10/2009 |
| WO | 2010091383 A2 | | 8/2010 |
| WO | WO 2012/084714 | * | 6/2012 |
| WO | 2013088327 A1 | | 6/2013 |

OTHER PUBLICATIONS

International Search Report and Written Opinion for International Application No. PCT/IB2014/000949 dated Jan. 20, 2015.
International Search Report and Written Opinion for International Application No. PCT/US2016/014397 dated May 9, 2016.
International Search Report and Written Opinion in corresponding application PCT/IB2012/057138, 14 pages, dated Feb. 28, 2013.
Office Action for Japanese Patent Application No. 2014-545447 dated Oct. 31, 2016 (includes English language translation).
Office Action for U.S. Appl. No. 14/364,060 dated Nov. 23, 2016.
Cohn, et al., The Evolution of Mitral Valve Surgery, Am heart Hosp. J. 2003:1 pp. 40-46 (2003).
Daimon, et al., Percutaneous Mitral Valve Repair for Chronic Ischemic Mitral Regurgitation. Journal of the American Heart Association, publ. Apr. 25, 2005.
DeSimone, et al., Adjustable Tricuspid Valve Annuloplasty Assisted by Intraoperative Transesophageal . . . The American Journal of Cardiology vol. 71 pp. 926-931 Apr. 15, 1993.
Felger, M.D. et al., Robot-Assisted Sutureless Minimally Invasive Mitral Valve Repair, Cardiovascular Surgery, Surgical Technology International XII, p. 185-187 (undated).
Folliguet, et al., Mitral valve repair robotic versus sternotomy, European Journal of Cardio-Thoracic Surgery 29 (2006) pp. 362-366.
Greelish et al., Minimally invasive mitral valve repair suggests earlier operations for mitral valve., The Journal of Thoracic & Cardiovascular Surgery vol. 126, No. 2 (2003).
Maniu, MD, et al. Acute & Chronic Reduction of Functional Mitral Regurgitation . . . Journal of the American College of Cardiology, vol. 44, No. 8, pp. 1652-1661 (2004).
International Search Report and Written Opinion for PCT/US20161014397 dated May 9, 2016.
CMC Rescue Catalog #127 p. 53 plus cover pages (2011).
Product literature for CMC rescue rack model No. 300890 (2012).

* cited by examiner

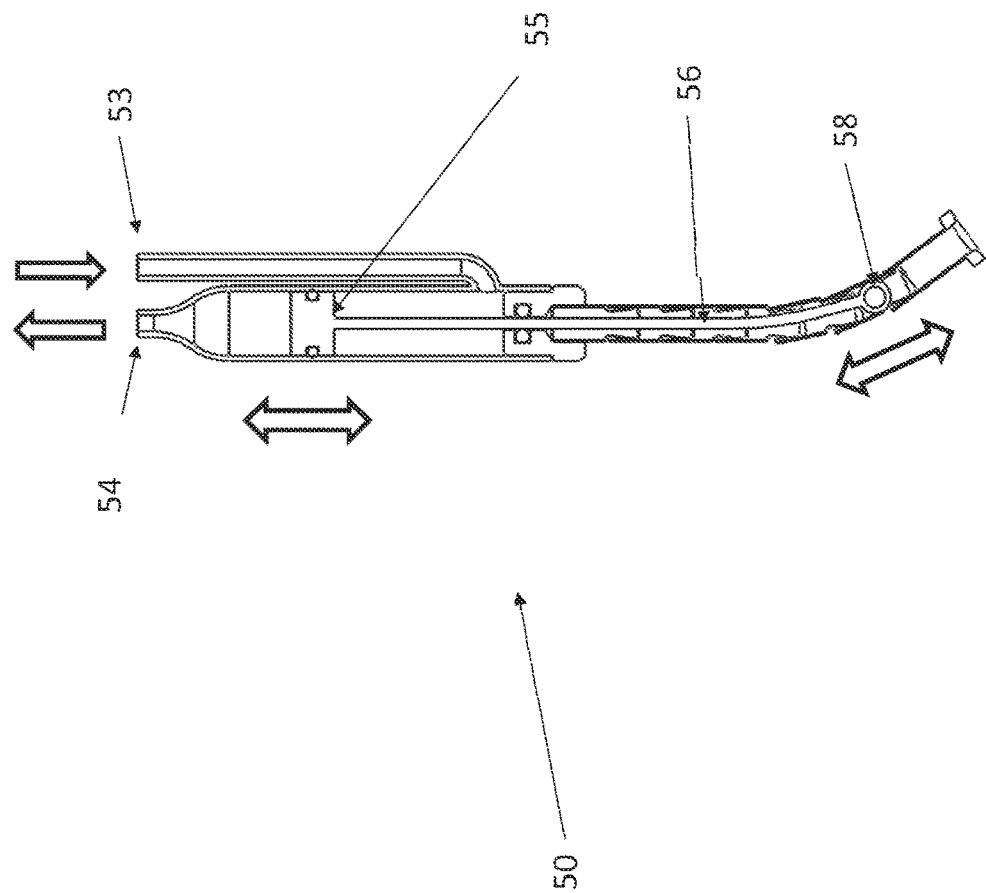

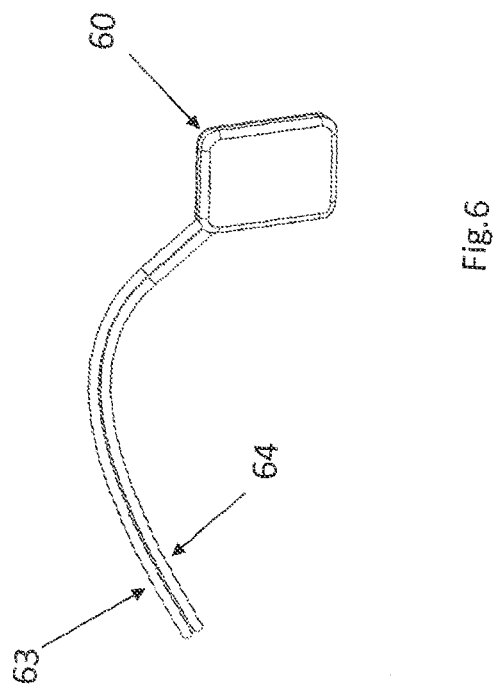
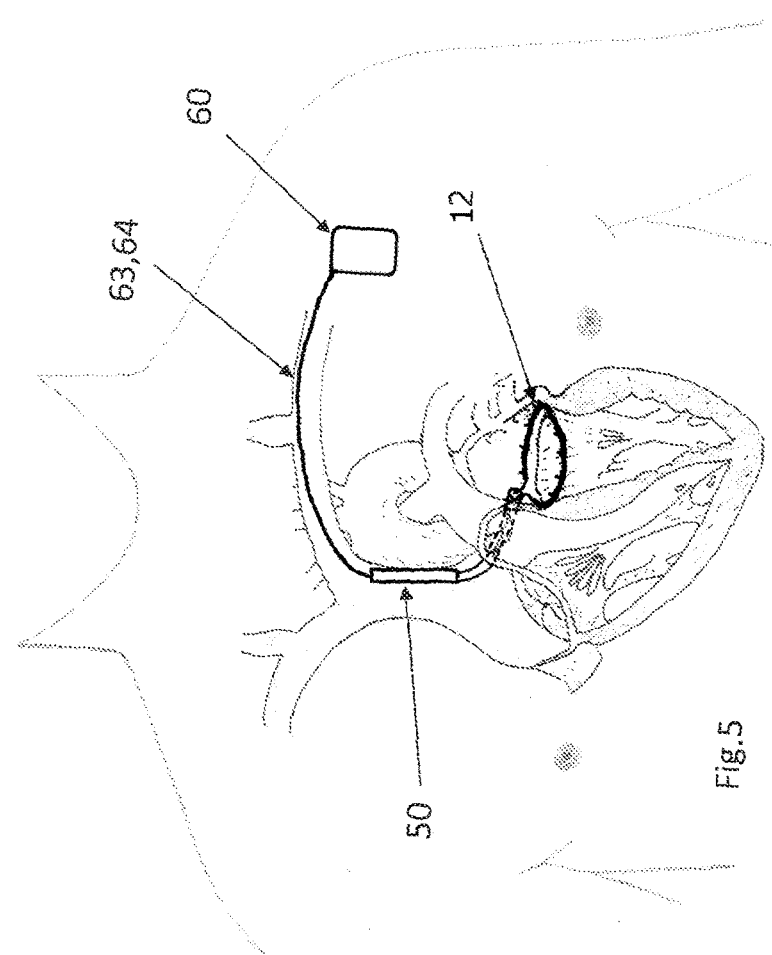

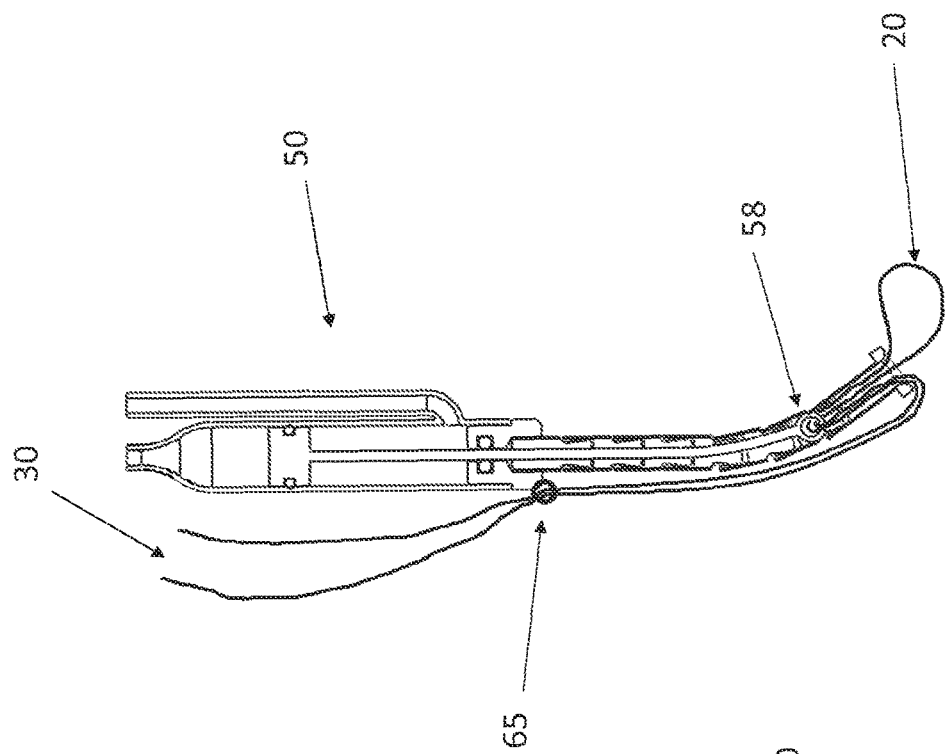
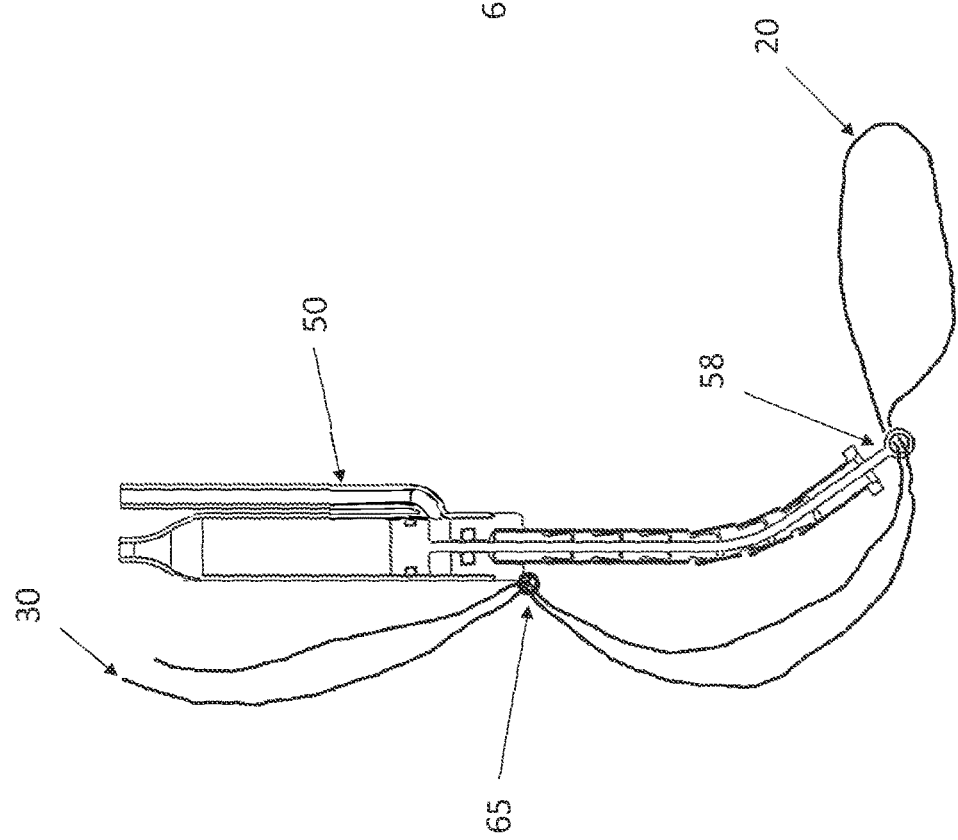

MAGNETICALLY COUPLED CINCHING OF A LOOP INSTALLED IN A VALVE ANNULUS

CROSS REFERENCE TO RELATED APPLICATIONS

This application claims the benefit of U.S. Provisional Application 62/107,437, filed Jan. 25, 2015; and this application is also a continuation-in-part of U.S. application Ser. No. 14/364,060, which is the US national phase of PCT/IB2012/057138, filed Dec. 10, 2012, which claims priority to both U.S. Provisional Application 61/683,736, filed Aug. 16, 2012, and U.S. Provisional Application 61/569,304, filed 12 Dec. 2011. Each of the above-identified applications is incorporated herein by reference in its entirety.

BACKGROUND

U.S. application Ser. No. 14/364,060, which published as US 2014/0309730 and is incorporated herein by reference in its entirety, describes implanting a tissue engaging member having a cinching loop that runs through the tissue engaging member on a mitral or tricuspid valve annulus, waiting for a tissue healing process to form a bond between the tissue engaging member and the annulus, and subsequently cinching the cinching loop to reduce the diameter of the annulus.

SUMMARY OF THE INVENTION

One aspect of the invention is directed to an apparatus for reducing a diameter of an annulus in a patient. This apparatus includes a tissue engaging member configured for installation on the annulus and an actuator configured for implantation into the patient's body. The tissue engaging member has a plurality of anchors configured to implant the tissue engaging member into the annulus, and a cinching loop that runs through the tissue engaging member. A first end of the cinching loop is connected to a first cinching wire and a second end of the cinching loop is connected to a second cinching wire. The actuator is configured to, when actuated, pull the first cinching wire and the second cinching wire in a proximal direction while holding a distal end of the first cinching wire in close proximity to a distal end of the second cinching wire, so as to cause a reduction in the diameter of the cinching loop. The actuator is further configured to be actuated from outside the patient's body after the actuator has been implanted in the patient's body.

In some embodiments, the actuator comprises a flexible tube that is non-compressible in a proximal-to-distal direction, with a diameter that is sufficiently small to hold the distal end of the first cinching wire in close proximity to the distal end of the second cinching wire. In some embodiments, the tissue engaging member has a toroidal outer surface configured to promote tissue ingrowth and an inner lumen, and the cinching loop runs through the inner lumen. In some embodiments, the first cinching wire, the cinching loop, and the second cinching wire are all formed from a single continuous braided cord. In some embodiments, the first cinching wire and the second cinching wire are affixed to the actuator using at least one of a knot and a clip.

In some embodiments, the apparatus also includes a cord lock configured to lock the first cinching wire and the second cinching wire to a fixed position on the actuator when the actuator is actuated. The cord lock may be implemented with an eyelet that moves in a distal to proximal direction and a plurality of sliding rollers configured to lock the first cinching wire and the second cinching wire into position when the eyelet moves proximally past a distalmost one of the sliding rollers.

In some embodiments, the actuator comprises a hydraulic cylinder having an inlet port and a pump configured to, when actuated, pump hydraulic fluid into the inlet port. Optionally, the pump may be rotary magnetic pump configured for implantation beneath the patient's skin, and this pump is configured to pump when a rotating magnetic field is coupled into the rotary magnetic pump. Optionally, the pump may be a reciprocating magnetic pump configured for implantation beneath the patient's skin, and this pump is configured to pump when a reciprocating magnetic field is coupled into the reciprocating magnetic pump.

In some embodiments, the actuator includes an electric motor configured for implantation beneath the patient's skin and a controller configured to operate the electric motor in response to receipt of a signal from outside the patient's body.

Another aspect of the invention is directed to a method for reducing a diameter of an annulus in a patient. This method includes the step of implanting a tissue engaging member on the annulus. The tissue engaging member has a plurality of anchors configured to implant the tissue engaging member into the annulus, and a cinching loop that runs through the tissue engaging member. A first end of the cinching loop is connected to a first cinching wire and a second end of the cinching loop is connected to a second cinching wire. This method also includes the step of implanting an actuator into the patient's body and connecting the actuator to the first cinching wire and the second cinching wire so that the actuator can pull the first cinching wire and the second cinching wire in a proximal direction while holding a distal end of the first cinching wire in close proximity to a distal end of the second cinching wire, so as to cause a reduction in the diameter of the cinching loop. This method also includes the step of actuating the actuator from outside the patient's body after the actuator has been implanted and connected.

In some embodiments, the step of implanting the actuator includes guiding a catheter over the cinching wires and subsequently delivering the actuator, via the catheter, to a desired position. In some embodiments, the tissue engaging member has an outer surface configured to promote ingrowth of tissue, and the method further includes the step of waiting for a tissue healing process to form a bond between the tissue engaging member and the annulus. The waiting step is implemented after the step of implanting the tissue engaging member and before the step of actuating the actuator. In some embodiments, the method also includes the step of affixing the first cinching wire and the second cinching wire to the actuator using at least one of a knot and a clip.

In some embodiments, the method also includes the step of affixing the first cinching wire and the second cinching wire to the actuator using a cord lock configured to lock the first cinching wire and the second cinching wire to a fixed position on the actuator when the actuator is actuated. Optionally, the step of affixing the first cinching wire and the second cinching wire to the actuator using a cord lock includes moving an eyelet in a distal-to-proximal direction until the eyelet is more proximal than a distalmost roller in a set of sliding rollers.

In some embodiments, the step of actuating the actuator comprises pumping a hydraulic fluid into the inlet port of a hydraulic cylinder. In some embodiments, the step of actuating the actuator comprises coupling at least one of a rotating magnetic field and a reciprocating magnetic field into the actuator. In some embodiments, the step of actuating the actuator includes activating an electric motor.

BRIEF DESCRIPTION OF THE DRAWINGS

FIG. 4 is a cross section of the FIG. 3 embodiment, with the piston retracted.

FIG. 5 shows a hydraulic pump connected to the actuator of FIG. 3.

FIG. 6 is a detail of the proximal portion of the FIG. 5 configuration.

FIG. 7A shows the actuator of FIG. 3 with the piston extended after the cinching wires have been affixed, FIG. 7B shows the actuator of FIG. 7A after the piston is retracted.

DESCRIPTION OF THE PREFERRED EMBODIMENTS

This application describes methods and apparatuses for implementing cinching using an actuator that is preferably implanted into the patient's body during the same procedure in which the tissue engaging member with the cinching loop is implanted.

Figure 1A:
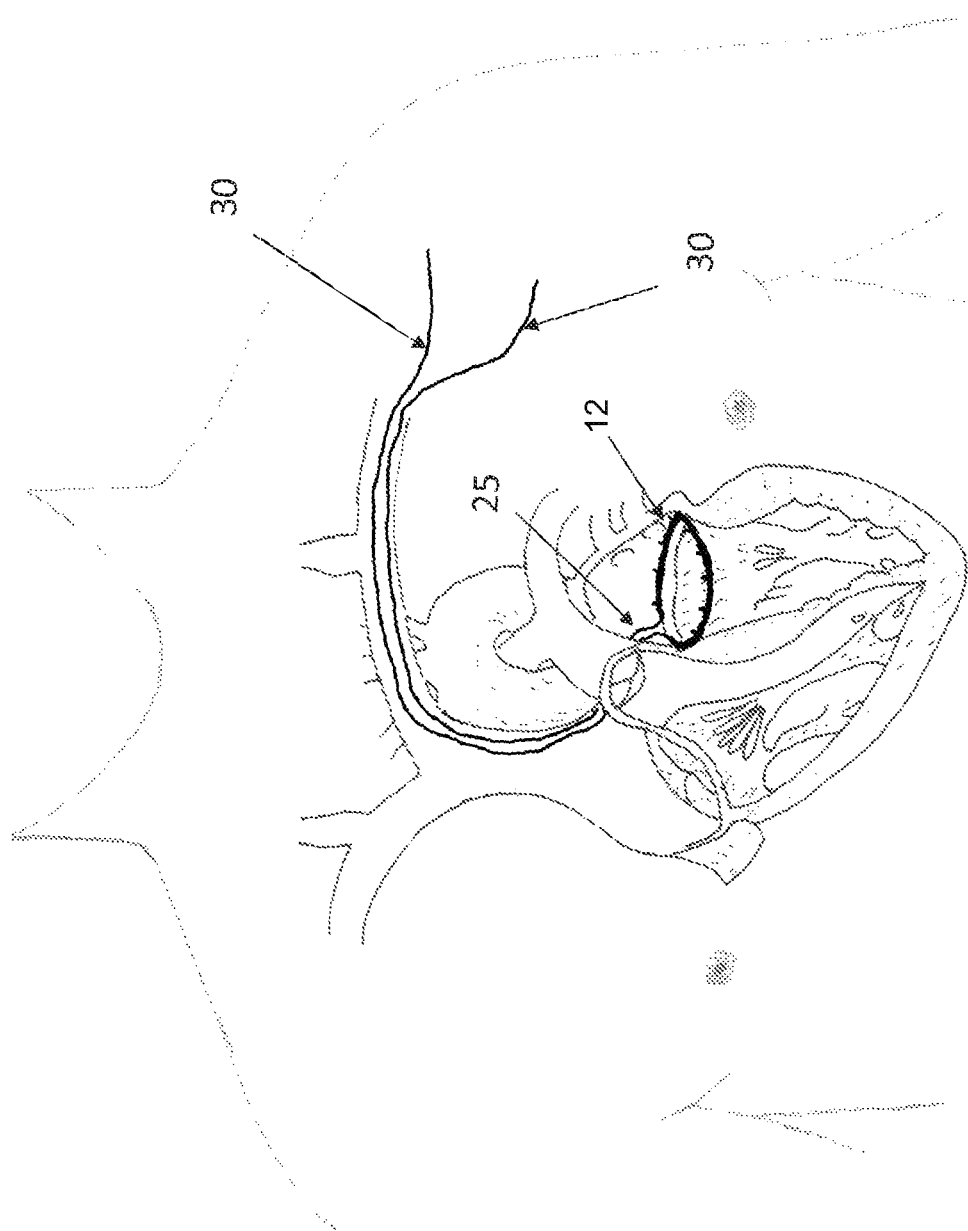
FIG. 1A depicts a tissue engaging member that has been implanted in the annulus of a mitral valve with cinching wires that terminate on the tissue engaging member.
Figure 1B:
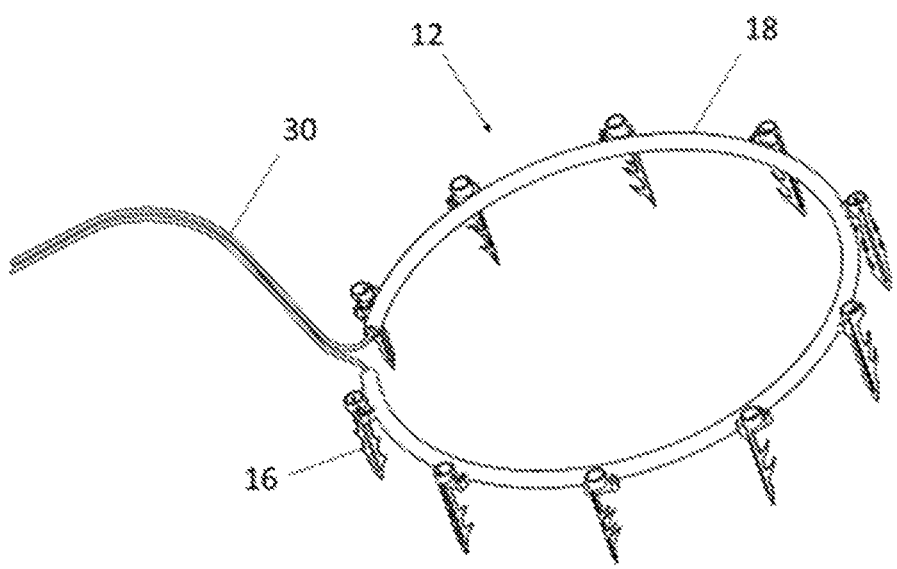
FIG. 1B is a detail of the tissue engaging member of FIG. 1A.

FIG. 1A depicts a situation in which a tissue engaging member 12 has already been implanted in the annulus of a mitral valve (which may be accomplished, e.g., using the apparatus described in the '060 application). FIG. 1B a detail of the tissue engaging member of FIG. 1A. In FIGS. 1A and 1B, access to the mitral valve annulus was previously obtained by venous access through the subclavian vein, and a trans-septal puncture was used to access the atrium side of the mitral valve annulus to install the tissue engaging member 12 in the depicted position. The tissue engaging member 12 preferably includes a loop of ingrowth promoting material 18 that is initially implanted on the annulus using a plurality of anchors 16. A cinching loop 20 runs through the tissue engaging member 12, and each end of the cinching loop 20 terminates on a cinching wire 30. Preferably, the first cinching wire, the cinching loop, and the second cinching wire are all formed from a single wire or a continuous braided cord. Note that as used herein, the term "wire" is not limited to metal wire, and it includes non-metallic wire-shaped structures. The term "wire" also includes different configurations for implementing wire, including solid wires, braided wires, and non-braided multifilament wires.

After the tissue engaging member 12 is implanted, the cinching wires 30 that terminate on the cinching loop 20 will follow the access path through which they were introduced. Thus, starting at the cinching loop 20, the cinching wires 30 will pass through the septum, into the vena cava, into the subclavian vein, and eventually will pass out of the patient's body. As a result, the cinching wires can be used to guide the delivery of a catheter that establishes a conduit between the outside of the patient's body and the interface 25 between the cinching wires 30 and the cinching loop 20. More specifically, the cinching wires 30 can be used to guide the catheter into position just like a conventional guide wire is used to guide a conventional catheter to a desired position.

Figure 2:
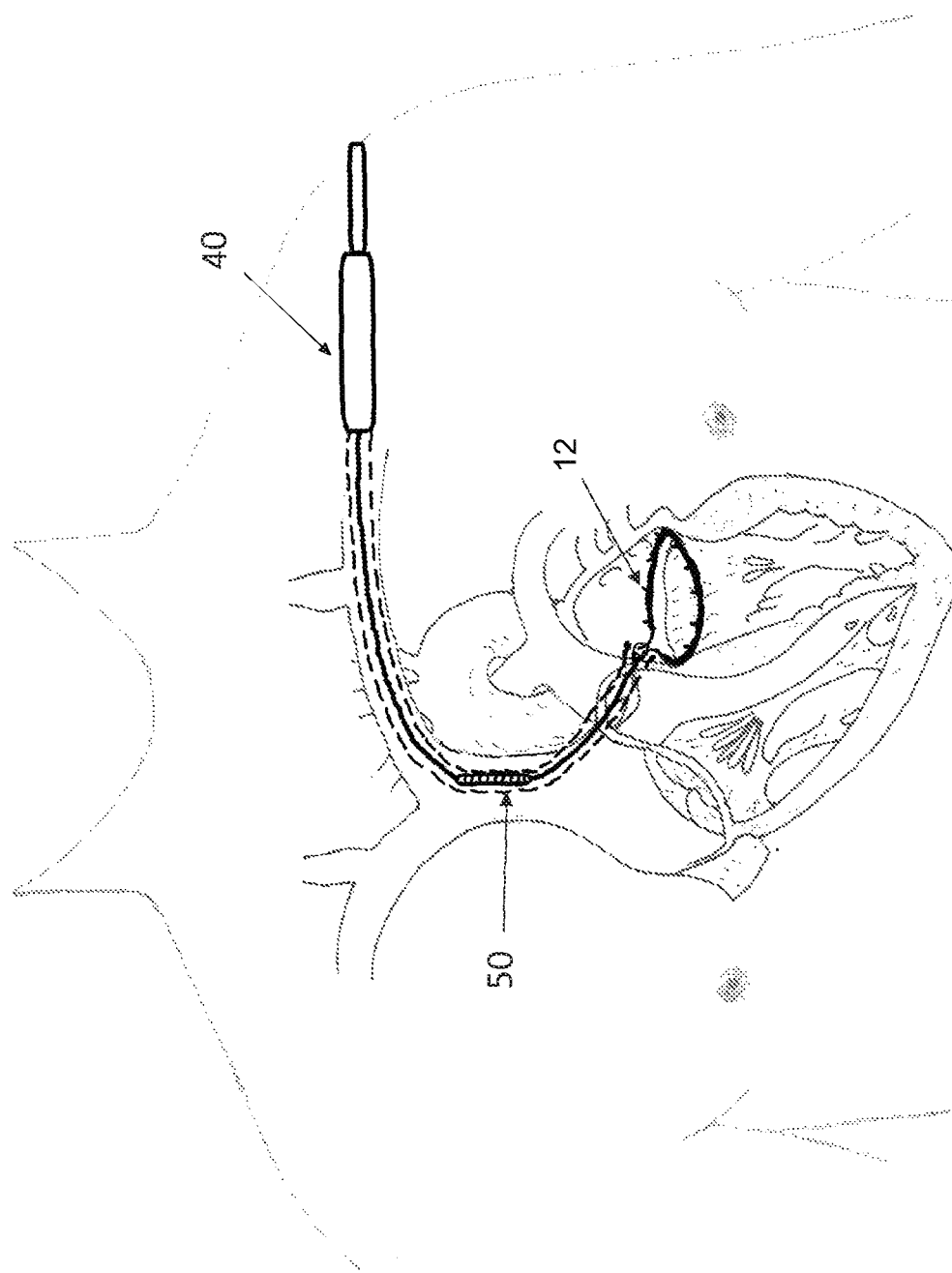
FIG. 2 depicts the FIG. 1A embodiment after a catheter that is positioned over the cinching wires.

FIG. 2 depicts such a catheter 40 that has been positioned between the outside of the patient's body and the interface 25. The portion of the catheter 40 that remains outside the patient's body is shown in solid lines, and the portion of the catheter 40 that is within the patient's body is shown in dashed lines. After the distal end of the catheter 40 is delivered to the interface 25 by pushing it along the cinching wires 30, an actuator 50 is delivered via the catheter 40 down to the interface 25. Before the actuator 50 is delivered via the catheter, the cinching wires 30 are preferably threaded through the eyelet 58 of the actuator (shown in FIG. 3), so that when the actuator 50 reaches the interface 25, it will appear as shown in FIG. 7A. In alternative embodiments, the use of the catheter 40 can be omitted, in which case the actuator can be delivered by pushing it along the cinching wires 30, with the cinching wires 30 serving as guide wires.

Figure 3:
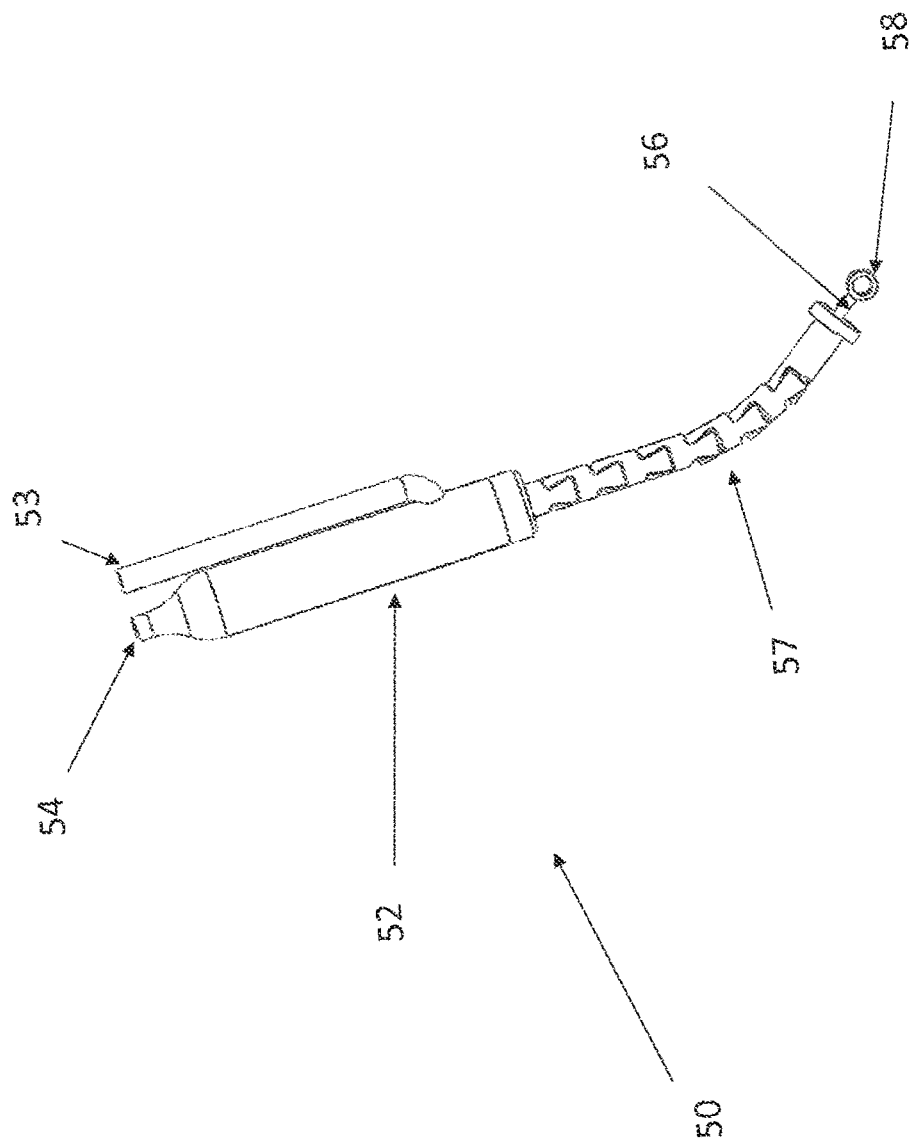
FIG. 3 depicts an actuator that includes a hydraulic cylinder, with the piston extended.

FIGS. 3 and 4 show one suitable approach for implementing the actuator 50 that uses a hydraulic cylinder 52. The hydraulic cylinder 52 has a fluid inlet 53 and a fluid outlet 54. Note that although the fluid inlet 53 and a fluid outlet 54 are depicted as separate tubes in the FIG. 3 embodiment, alternative configurations for the fluid inlet and fluid outlet may be used. For example, the fluid inlet or outlet may be implemented as a concentric cylinder that surround the body of the actuator 50.

A flexible tube 57 that resists compression in a proximal—distal direction is affixed to the distal end of the hydraulic cylinder 52. A piston 55 is disposed in the hydraulic cylinder 52 and the hydraulic cylinder 52 is configured so that when fluid is pumped into the inlet 53, the piston 55 will move in a proximal direction. When the piston travels proximally, the piston 55 will pull the cable 56 in a proximal direction, which pulls the eyelet 58 in a proximal direction. Initially, when the piston 55 is in its distal-most position, the eyelet 58 extends distally beyond the end of the flexible tube 57 (as seen in FIG. 3). When the piston 55 moves proximally, it will pull the eyelet 58 into the flexible tube 57 (as seen in FIG. 4).

The actuator 50 is delivered to the interface 25 via the catheter 40, so that the cinching wires 30 pass through the eyelet 58 near the interface 25 (as shown in FIG. 7A). The cinching wires 30 are then preferably fastened to the body of the actuator 50 (e.g., at fastening point 65) or to a component that is proximal to the actuator 50 (e.g., using an appropriate fastener, clamp, knot, etc.). After the cinching wires 30 have been fastened, the portion of the cinching wires 30 that is proximal to the fastening point 65 may be severed and removed. Preferably, when the actuator 50 is initially delivered it to this position, a fluid inlet tube 63 and a fluid outlet tube 64 are connected to the fluid inlet 53 and the fluid outlet 54 respectively. Those tubes 63, 64 run in a proximal direction back along the catheter 40.

After the actuator is delivered and connected to the cinching wires 30, the catheter is removed. Turning now to FIGS. 5 and 6, a hydraulic pump 60 is connected at the proximal end of the fluid inlet tube 63 and the fluid outlet tube 64. The pump 60 is configured so that when the pump 60 is actuated, it will pump fluid into the fluid inlet tube 63. Preferably, the pump 60 is implanted inside the patient's body (e.g., just beneath the patient's skin). The pump is preferably configured so that the pump can be actuated from outside the patient's body. One suitable approach for implementing this without implanting a battery inside the pump is to use magnetic coupling to couple a rotating magnetic field into the pump. The pump contains a magnetic driver that is activated by this rotating magnetic field, and is configured to pump the fluid into the fluid inlet 63 when the rotating magnetic field is applied. The theory of operation of the magnetic coupling between the rotating magnetic field is similar to the coupling that is used in conventional magnetic stirrers.

In alternative embodiments, a reciprocating magnetic field may be used in place of the alternating magnetic field described above, and suitable modifications to the pump 60 would be made to make the pump respond to an externally applied reciprocating magnetic field.

In other alternative embodiments (not shown), instead of relying on the magnetic coupling described above, an electrical pump may be used. In this case, the system preferably relies on inductive coupling to provide power for the electrical pump. In other less preferred alternative embodiments, the pump may be battery operated, in which case a battery is also implanted.

In alternative (less preferred) embodiments, the inlet and outlet tube 63, 64 may pass through the patient's skin, and an external pump 60 may be used.

In other alternative embodiments (not shown), an electrically actuated actuator is used in place of the actuator 50 that relies on a hydraulic cylinder. Examples of suitable electrically actuated actuators that may be used to pull the cable 56 in a proximal direction include a rotary motor that turns a screw, a linear motor, and a solenoid. When any of these electrical systems are used in place of the hydraulic system described above, suitable modifications must be made. For example, instead of running inlet and outlet tubes 63, 64 down to the actuator, insulated wires would be used to deliver power to the actuator.

Turning now to FIGS. 7A and 7B, when the pump 60 is activated by the externally applied magnetic field, fluid is pumped into the fluid inlet tube 63, and it will travel into the fluid inlet 53 of the actuator 50. This will cause the piston 55 in the actuator 50 to rise. This will pull up on the cable 56, which will pull the eyelet 58 up into the flexible tube 57, and move the eyelet 58 from the position depicted in FIG. 7A to the position depicted in FIG. 7B. Because the eyelet 58 is attached to the cinching wires 30 at the interface 25, and the cinching wires 30 are fastened to the body of the actuator 50 at fastening point 65 (or to another component located proximally of the actuator 50) the eyelet 58 will pull a midsection the cinching wires 30 up into the flexible tube 57. The distal end of the flexible tube 57 is preferably non-compressible in a proximal-to-distal direction, and preferably has a small diameter that holds the two cinching wires 30 in close proximity. As a result, pulling the midsection the cinching wires 30 up will be reducing the diameter of the portion of the cinching loop that that is installed on the valve annulus, as seen (to an exaggerated degree) in FIG. 7B. This will tighten the annulus.

Preferably, the pump 60 is not actuated until the tissue engaging member 12 is securely embedded in the mitral valve annulus. The embedding of the tissue engaging member 12 into the annulus may be assisted by tissue healing, which can take a few weeks to occur. In this case, the pump 60 is preferably not actuated until after the time required for tissue healing to occur has elapsed (e.g., 2-3 months after the tissue engaging member 12 has been implanted). In alternative embodiments, the pump 60 may be actuated at other intervals, (e.g. a few days after the tissue engaging member 12 is implanted, months later, or even immediately after the tissue engaging member 12 is implanted).

Figure 8A:
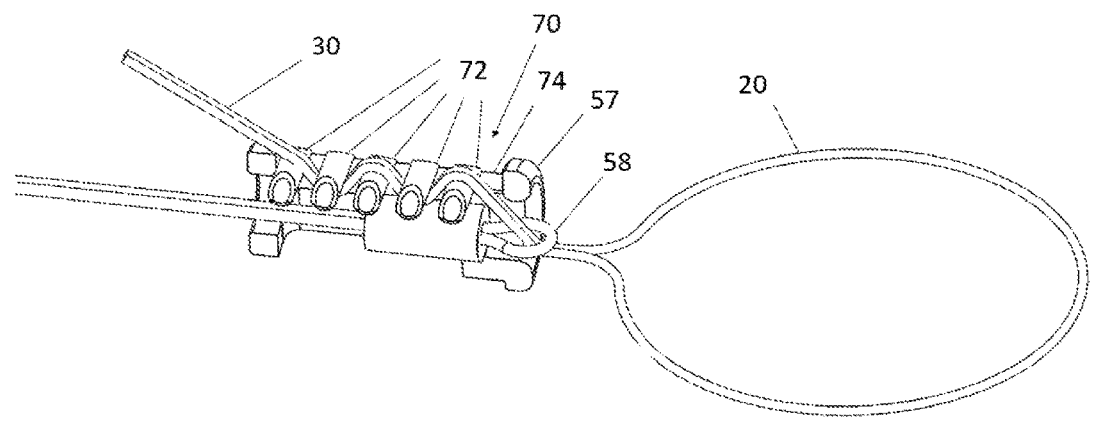
FIG. 8A depicts an automatic cord lock in an initial position.
Figure 8B:
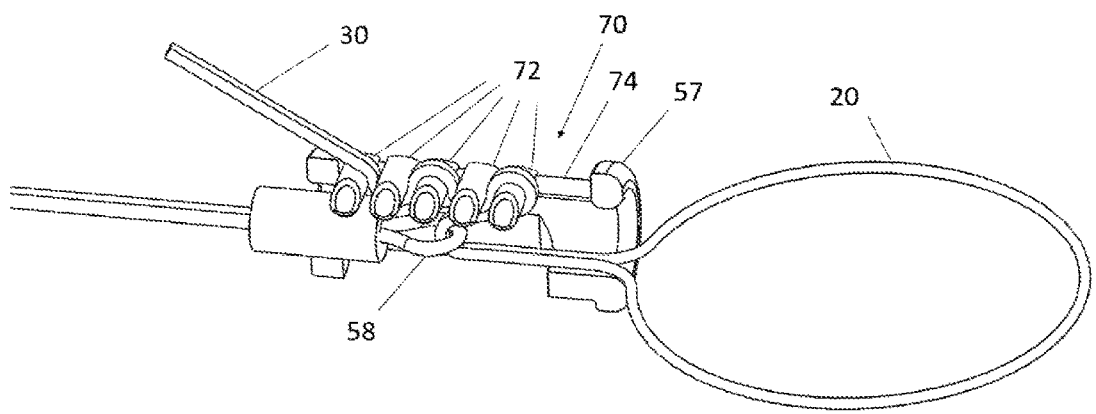
FIG. 8B depicts the automatic cord lock of FIG. 8A in an intermediate position.
Figure 8C:
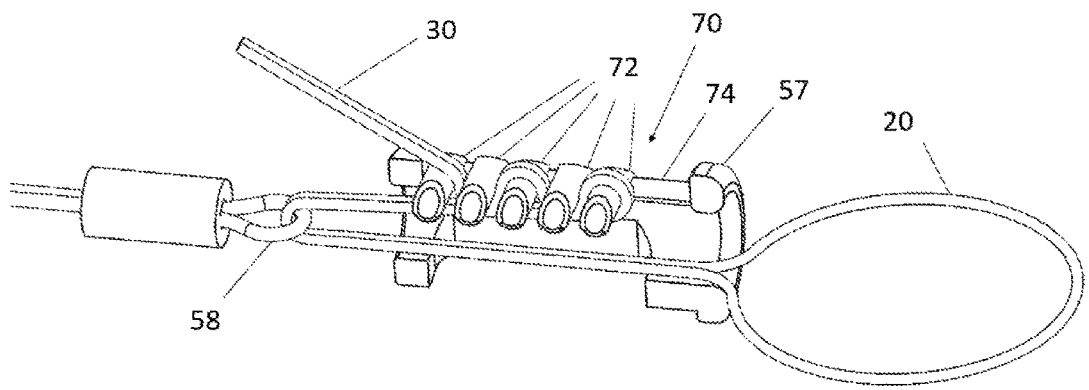
FIG. 8C depicts the automatic cord lock of FIG. 8A in a final position.

FIGS. 8A-8C depict an automatic cord lock 70 configured to lock the cinching wires 30 to a fixed position on the actuator. The operating principles of this automatic cord lock is similar to the "rescue rack" brake bar system that is used by mountain climbers. The automatic cord lock 70 includes a plurality of rollers 72 that are free to move back and forth in a proximal-distal direction within a track 74, but constrained from moving in other directions by the track 74.

Before installation of the actuator 50 with the cord lock 70, the cinching wires 30 have previously been positioned within the patient's anatomy (e.g., as shown in FIG. 1A). The cinching wires are pulled tight, and threaded in a zigzag fashion through adjacent rollers 72 as seen in FIG. 8A. The physician then slides the actuator 50 down over the cinching wires 30. In this step, the cinching wires 30 serve as guide wires to bring the actuator 50 to its final destination in the vicinity of the cinching loop 20, as seen in FIG. 8A. Note that because the rollers 72 are spaced relatively far apart at this stage, the cord lock 70 will not be locked, so it is possible to slide the actuator 50 in a distal direction until it reaches its desired destination.

When the time eventually arrives to initiate cinching (e.g., three months later), cord lock 70 can be switched into its locked position by actuating the actuator 50. When the actuator is actuated, the eyelet 58 (shown in FIGS. 3 and 4) is pulled backwards into the thrust tube 57. The eyelet 58 will pull the cinching wires 30 in a proximal direction until the eyelet 58 moves proximally beyond the distal-most roller 72. This will cause the rollers 72 to move closer together to one another which will lock the cord lock 70, as seen in FIG. 8B. Once the cord lock 70 is locked, further motion of the eyelet 58 will pull on the cinching wires 30 which will pull on the cinching loop 20. The end of the thrust tube 57 holds the first cinching wire 30 in close proximity to the second cinching wire 30, so that when the cinching wires 30 are pulled in a proximal direction, the cinching loop 20 will shrink, as shown in FIG. 8C. Because the cinching loop 20 runs through the tissue engaging member 12 (shown in FIGS. 1A and 1B), this will reduce the diameter of the annulus.

Figure 9:
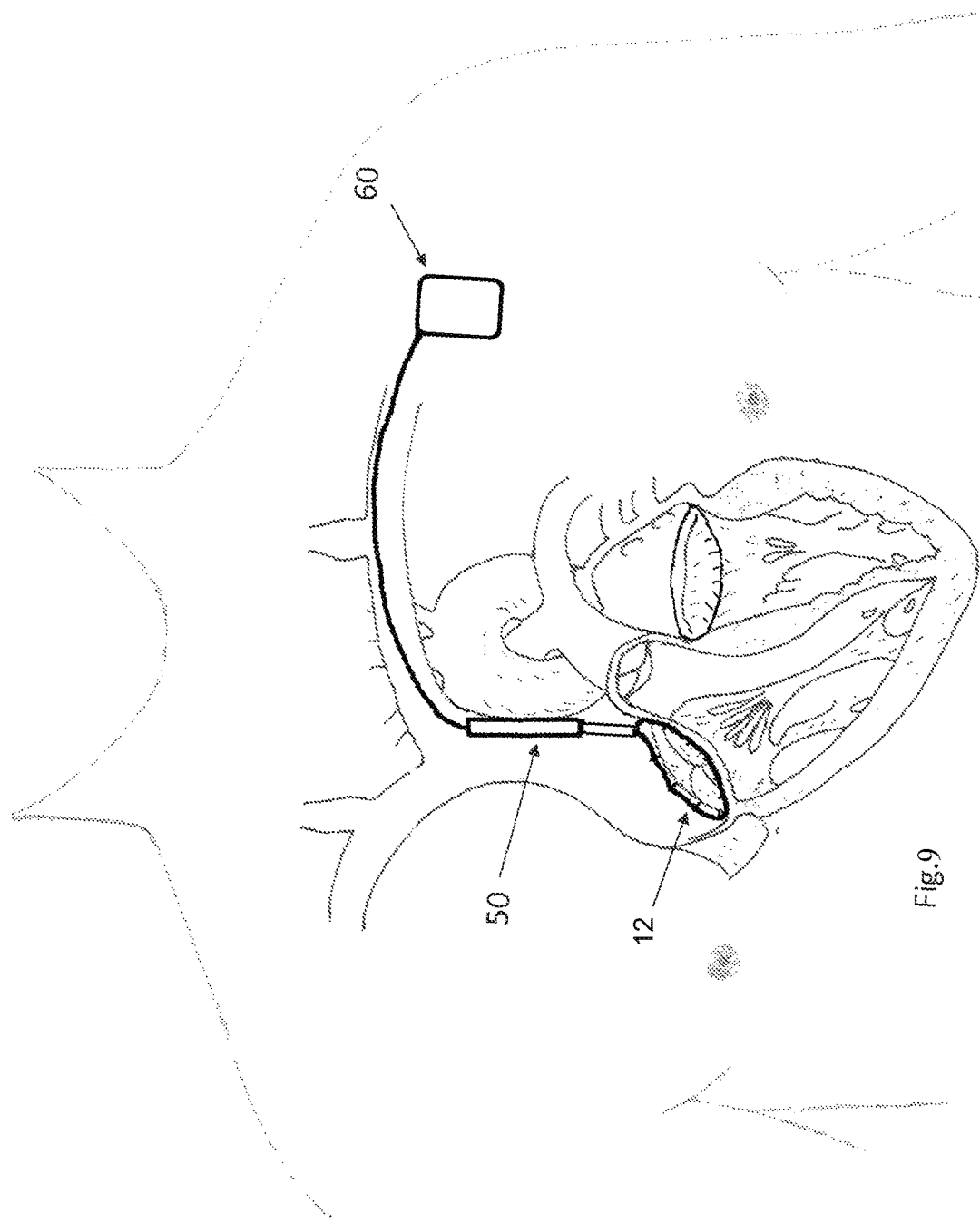
FIG. 9 depicts a tissue engaging member that is installed on the tricuspid valve annulus.

Note that while the invention is described and depicted above in the context of a tissue engaging member 12 that has been installed on the mitral valve annulus by accessing that annulus transseptally via the subclavian vein and the superior vena cava, the same procedures may be used when alternative approaches to the mitral annulus are taken (e.g., approaching via the inferior vena cava or approaching via the jugular vein and the superior vena cava). Similar procedures may also be used to tighten any tissue engaging member installed on any annulus in the body. For example, FIG. 9 depicts a tissue engaging member that is installed on the tricuspid valve annulus.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

We claim:

1. An apparatus for reducing a diameter of an annulus in a patient, the apparatus comprising:
    a tissue engaging member configured for installation on the annulus, the tissue engaging member having a plurality of anchors configured to implant the tissue engaging member into the annulus, and a cinching loop that runs through the tissue engaging member, wherein a first end of the cinching loop is connected to a first cinching wire and wherein a second end of the cinching loop is connected to a second cinching wire; and
    an actuator configured for implantation into the patient's body, wherein the actuator includes a component through which the first cinching wire and the second cinching wire are threaded and wherein the actuator is configured to, when actuated, pull the first cinching wire and the second cinching wire in a direction that faces away from the annulus while holding a distal end of the first cinching wire in close proximity to a distal end of the second cinching wire, so as to cause a reduction in the diameter of the cinching loop,
    wherein the actuator is further configured to be actuated from outside the patient's body after the actuator has been implanted in the patient's body.

2. The apparatus of claim 1, wherein the tissue engaging member has a toroidal outer surface configured to promote tissue ingrowth and an inner lumen, and wherein the cinching loop runs through the inner lumen.

3. The apparatus of claim 1, wherein the first cinching wire, the cinching loop, and the second cinching wire are all formed from a single continuous braided cord.

4. The apparatus of claim 1, wherein the first cinching wire and the second cinching wire are affixed to the actuator using at least one of a knot and a clip.

5. The apparatus of claim 1, further comprising a cord lock configured to lock the first cinching wire and the second cinching wire to a fixed position on the actuator when the actuator is actuated.

6. The apparatus of claim 5, wherein the cord lock comprises: an eyelet that moves in a distal to proximal direction; and a plurality of sliding rollers configured to lock the first cinching wire and the second cinching wire into position when the eyelet moves proximally past a distalmost one of the sliding rollers.

7. The apparatus of claim 1, wherein the actuator comprises a hydraulic cylinder having an inlet port and a pump configured to, when actuated, pump hydraulic fluid into the inlet port.

8. The apparatus of claim 7, wherein the pump comprises a rotary magnetic pump configured for implantation beneath the patient's skin, and wherein the rotary magnetic pump is configured to pump when a rotating magnetic field is coupled into the rotary magnetic pump.

9. The apparatus of claim 7, wherein the pump comprises a reciprocating magnetic pump configured for implantation beneath the patient's skin, and wherein the reciprocating magnetic pump is configured to pump when a reciprocating magnetic field is coupled into the reciprocating magnetic pump.

10. The apparatus of claim 1, wherein the actuator comprises: an electric motor configured for implantation beneath the patient's skin; and a controller configured to operate the electric motor in response to receipt of a signal from outside the patient's body.

11. The apparatus of claim 1, wherein the component through which the first cinching wire and the second cinching wire are threaded comprises an eyelet.

12. An apparatus for reducing a diameter of an annulus in a patient, the apparatus comprising:
    a tissue engaging member configured for installation on the annulus, the tissue engaging member having a plurality of anchors configured to implant the tissue engaging member into the annulus, and a cinching loop that runs through the tissue engaging member, wherein a first end of the cinching loop is connected to a first cinching wire and wherein a second end of the cinching loop is connected to a second cinching wire; and
    an actuator configured for implantation into the patient's body, wherein the actuator is configured to, when actuated, pull the first cinching wire and the second cinching wire in a direction that faces away from the annulus while holding a distal end of the first cinching wire in close proximity to a distal end of the second cinching wire, so as to cause a reduction in the diameter of the cinching loop,
    wherein the actuator is further configured to be actuated from outside the patient's body after the actuator has been implanted in the patient's body, and
    wherein the actuator comprises a flexible tube that is non-compressible in a proximal-to-distal direction, with a diameter that is sufficiently small to hold the distal end of the first cinching wire in close proximity to the distal end of the second cinching wire.

13. A method for reducing a diameter of an annulus in a patient, the method comprising the steps of:
    implanting a tissue engaging member on the annulus, the tissue engaging member having a plurality of anchors configured to implant the tissue engaging member into the annulus, and a cinching loop that runs through the tissue engaging member, wherein a first end of the cinching loop is connected to a first cinching wire and wherein a second end of the cinching loop is connected to a second cinching wire;
    threading the first cinching wire and the second cinching wire through a portion of an actuator;
    implanting the actuator into the patient's body and connecting the actuator to the first cinching wire and the second cinching wire so that the actuator can pull the first cinching wire and the second cinching wire in a direction that faces away from the annulus while holding a distal end of the first cinching wire in close proximity to a distal end of the second cinching wire, so as to cause a reduction in the diameter of the cinching loop; and
    actuating the actuator from outside the patient's body after the actuator has been implanted and connected.

14. The method of claim 13, wherein the step of implanting the actuator comprises guiding a catheter over the cinching wires and subsequently delivering the actuator, via the catheter, to a desired position.

15. The method of claim 13, wherein the tissue engaging member has an outer surface configured to promote ingrowth of tissue, and wherein the method further comprises the step of waiting for a tissue healing process to form a bond between the tissue engaging member and the annulus, wherein the waiting step is implemented after the step of implanting the tissue engaging member and before the step of actuating the actuator.

16. The method of claim 13, further comprising the step of affixing the first cinching wire and the second cinching to the actuator using at least one of a knot and a clip.

17. The method of claim 13, further comprising the step of affixing the first cinching wire and the second cinching to the actuator using a cord lock configured to lock the first cinching wire and the second cinching wire to a fixed position on the actuator when the actuator is actuated.

18. The method of claim 17, wherein the step of affixing the first cinching wire and the second cinching to the actuator using a cord lock comprises moving an eyelet in a distal-to-proximal direction until the eyelet is more proximal than a distalmost roller in a set of sliding rollers.

19. The method of claim 13, wherein the step of actuating the actuator comprises pumping a hydraulic fluid into the inlet port of a hydraulic cylinder.

20. The method of claim 19, wherein the step of actuating the actuator comprises coupling at least one of a rotating magnetic field and a reciprocating magnetic field into the actuator.

21. The method claim 20, wherein the step of actuating the actuator comprises activating an electric motor.

\* \* \* \* \*